United States Patent [19]

Brandestini et al.

[11] Patent Number: 4,766,704
[45] Date of Patent: Aug. 30, 1988

[54] METHOD AND APPARATUS FOR THE CUSTOM SHAPING OF DENTAL INLAYS, ONLAYS, CROWNS, BRIDGES AND PARTS THEREOF

[76] Inventors: Marco Brandestini, 10 Gartenstr CH-8702, Zollikon; Werner H. Moermann, 57 Zweiackerstrasse, CH-8053 Zuerich, both of Switzerland

[21] Appl. No.: 790,294

[22] Filed: Oct. 22, 1985

[30] Foreign Application Priority Data

Oct. 24, 1984 [CH] Switzerland ............. 05 089/84

[51] Int. Cl.⁴ .................................. B24B 1/00
[52] U.S. Cl. ........................... 51/327; 51/5 D; 51/281 R
[58] Field of Search ............. 51/281 R, 283 R, 327, 51/5 R, 5 D, 284 R, 326, 165.71

[56] References Cited

U.S. PATENT DOCUMENTS

| | | | |
|---|---|---|---|
| 2,423,367 | 7/1947 | Bolender | 51/105 |
| 2,697,878 | 12/1954 | Oberley | 32/59 |
| 3,570,193 | 3/1971 | Barrett | 51/173 |
| 4,137,677 | 2/1979 | Nedreski | 51/165.77 |
| 4,193,228 | 3/1980 | Bowler | 51/170 T |
| 4,233,782 | 11/1980 | Perrault | 51/5 R |
| 4,274,231 | 6/1981 | Verega | 51/5 D |
| 4,385,360 | 5/1983 | Yamada | 364/514 |
| 4,411,626 | 10/1983 | Becker | 433/223 |
| 4,575,805 | 3/1986 | Moermann et al. | 364/474 |
| 4,611,288 | 9/1986 | Duret | 364/474 |
| 4,615,678 | 10/1986 | Moermann | 433/201.1 |

FOREIGN PATENT DOCUMENTS

| | | |
|---|---|---|
| 1502515 | 2/1969 | Fed. Rep. of Germany . |
| 1902015 | 8/1970 | Fed. Rep. of Germany . |
| 57-173447 | 10/1982 | Japan . |
| 563837 | 8/1944 | United Kingdom . |
| 891330 | 3/1959 | United Kingdom . |
| 1114929 | 5/1968 | United Kingdom . |

*Primary Examiner*—Frederick R. Schmidt
*Assistant Examiner*—Robert R. Rose
*Attorney, Agent, or Firm*—Flynn, Thiel, Boutell & Tanis

[57] ABSTRACT

A method and apparatus for machining a custom-shaped dental restorative part from a blank of dental material yield the entire part in a single operation, and include a workpiece being mounted on a support member which facilitates rotation and axial movement of the workpiece. A separating disk is used for almost the entire machining operation, and an additional tool in the shape of a burr can optionally be provided to shape more elaborate pieces. The disk and burr are supported by a tool holder which is supported for movement parallel to and rotationally about an axis. The disk and burr are powered by a closed loop fluid supply arrangement. A tool velocity sensing scheme is utilized for adaptive feed and to compensate for tool wear. The machining mechanism and associated control circuitry are enclosed in a common cabinet so as to provide a mobile unit suitable for use in a dentist's office.

23 Claims, 8 Drawing Sheets

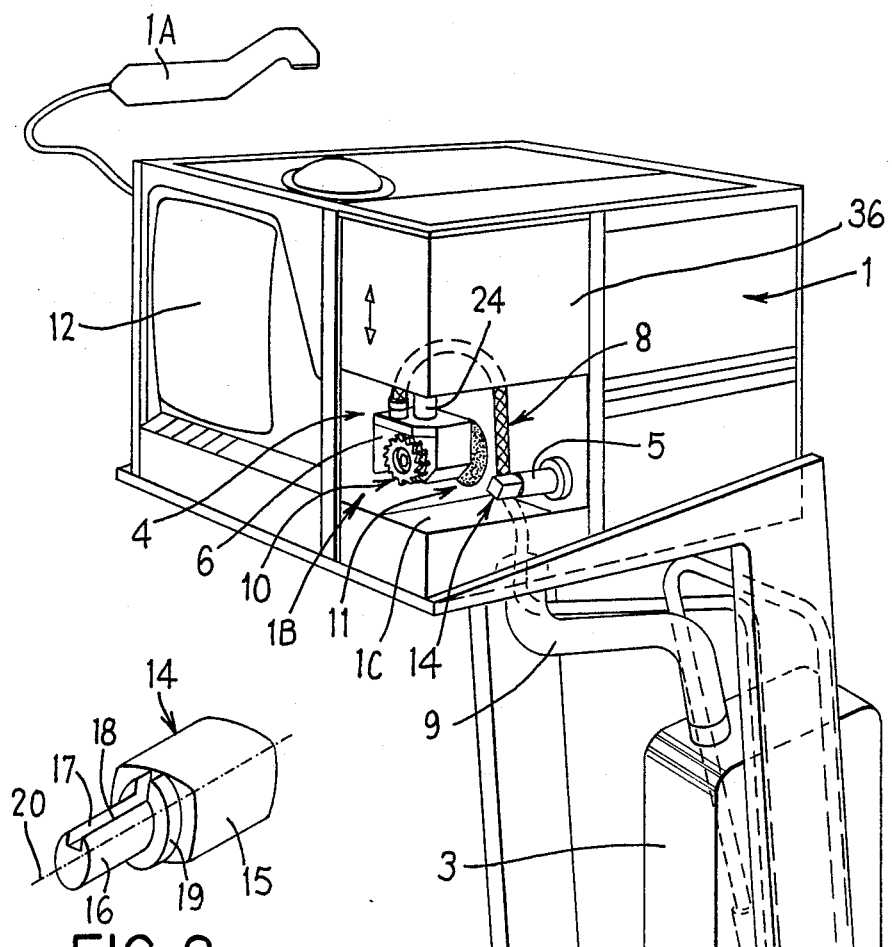
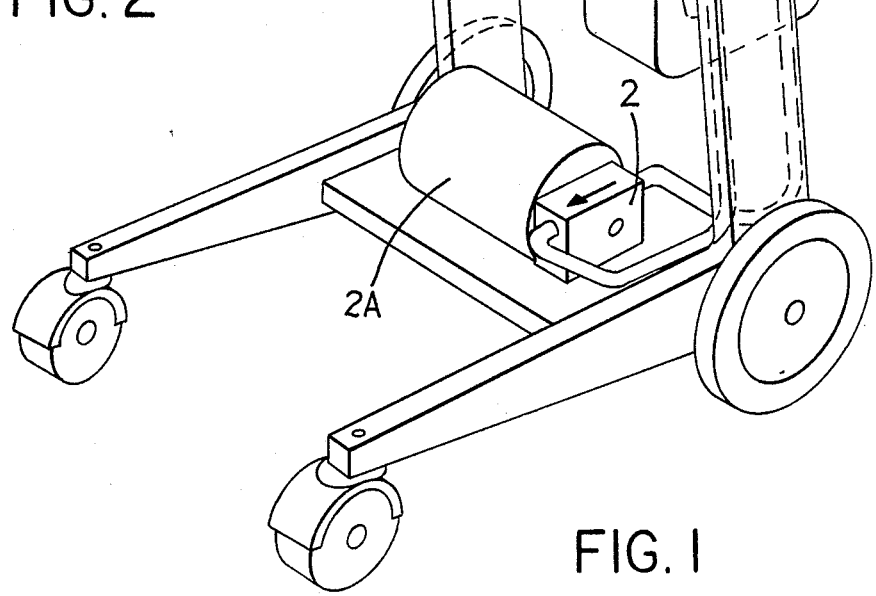
FIG. 2
FIG. 1

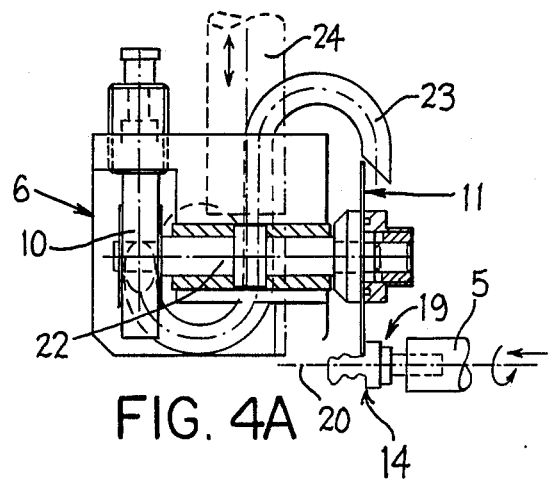
FIG. 4A
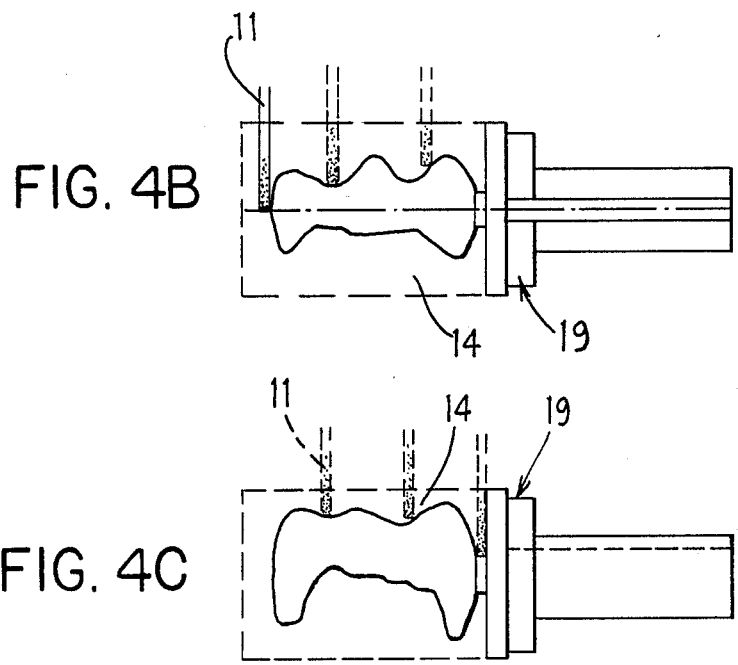
FIG. 4B
FIG. 4C

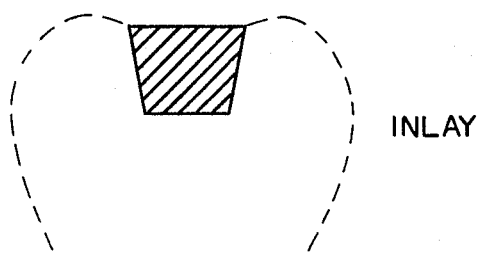
FIG. 9A  INLAY
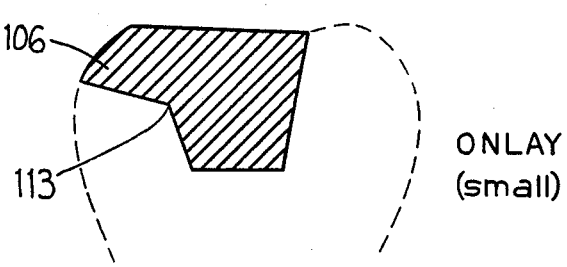
FIG. 9B  ONLAY (small)
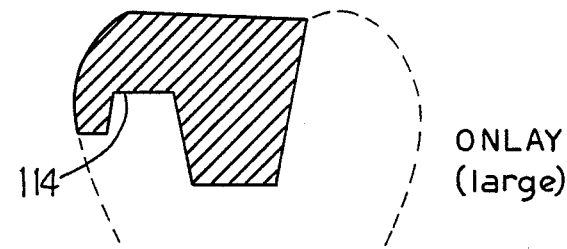
FIG. 9C  ONLAY (large)
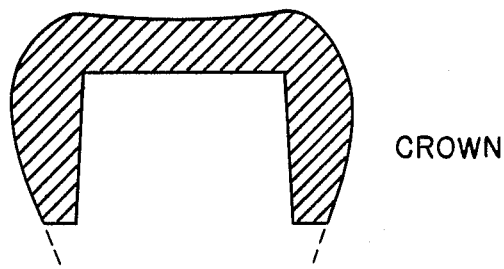
FIG. 9D  CROWN

METHOD AND APPARATUS FOR THE CUSTOM SHAPING OF DENTAL INLAYS, ONLAYS, CROWNS, BRIDGES AND PARTS THEREOF

CROSS-REFERENCE TO RELATED PATENTS

The subject matter of this application is related to the subject matter of Applicants' U.S. Pat. Nos. 4,575,805 and 4,615,678.

FIELD OF THE INVENTION

This invention relates to an improved method and apparatus for automatically machining from a workpiece an implant which will fit into a cavity in a tooth.

BACKGROUND OF THE INVENTION

The present invention relates to the art of dental restoration. Presently, all dental work is done using the age-old casting/lost wax technique. Efforts are underway to replace this method, as well as direct filling techniques, by utilizing modern technology such as three-dimensional data acquisition and computer controlled milling devices. The applicants' above-mentioned U.S. Pat. No. 4,575,805 teaches such a scheme. Devices have been developed which can machine uniquely shaped items, for example as disclosed in Yamada U.S. Pat. No. 4,385,360 and Duret European publication No. 91 876, which corresponds to Duret U.S. Pat. No. 4,611,288. Becker European publication No. 33 492 which corresponds to U.S. Pat. No. 4,411,626, teaches the fabrication of the desired dental pieces, but requires an intermediate step, namely the machining of a wax model. It should be noted that, to date, the issue of shaping hard dental materials within the time frame set by a dentist's schedule has not been specifically addressed. Grinding machines of the type typically found on a factory floor could well machine the desired materials, for example machines of the type disclosed in Bolender U.S. Pat. No. 2,423,367, Wies German Offenlegungsschrift No. 15 02 515, and Kondou Japanese Pat. No. 57-173447. Such devices all use grinding wheels in one way or another, but none can be adapted for the particular size requirements of a dental implant, nor to shape the implant all over as required according to the present invention. Other systems such as those disclosed in Reid British Pat. No. 1 114 929 and Torit British Pat. No. 891 330 are adapted to do finishing only; in other words the parts are already in a semi-finished form and are merely polished, deflashed or trimmed.

It is therefore an object of the present invention to provide to the dentist a small and affordable unit which allows the fabrication of dental restorative parts in a single session with a patient.

It is a further object to arrange this unit in a way which eliminates manual changing of tools and re-clamping of the workpiece or other operator interaction during the machining process.

It is yet another object of the invention to make the system self-calibrating, or in other words to make it automatically compensate for tool wear.

A principal object is to provide a machine which can shape the hard ceramic materials ideally suited to the oral environment in a matter of a few minutes and without the need of extended manual trimming. Initially, an apparatus which utilizes a small diamond burr of the type dentists commonly use in hand-held instruments would seem to fulfill the requirements. However, due to the much larger volume of material to be machined, and the fact that a natural tooth, apart from its enamel exterior, is relatively soft and that in any event the dentist tends to remove mainly decayed material, the diamond burr is not suited for the specific job. Another consideration is the high speed required to drive a tool with a diameter this small. A cavity is typically contoured in a minute or two, and the hand-held turbine can in any event be replaced if excessive wear occurs. In contrast, the invention requires a machine which should ideally be able to operate for many hours without maintenance. While the restoration can be made from metallic alloys, public demand calls for white, tooth-like inlays which restore the tooth both functionally and aesthetically. Ceramic or composite materials (acrylics loaded with inorganic matter) best meet these requirements

SUMMARY OF THE INVENTION

According to the invention, a method of fabricating an implant for a cavity in a tooth includes the step of machining on a workpiece a three-dimensional surface corresponding in shape to the cavity, the workpiece preferably being completely machined without removing or reclamping the workpiece during the machining process. One preferred form of the inventive method includes the steps of simultaneously rotating the workpiece about a first axis, rotating a grinding disk of small axial thickness continuously about a second axis parallel to and spaced from said first axis and at a speed substantially greater than the speed at which the workpiece is rotated, moving the disk relative to the workpiece in a direction parallel to the first axis, and selectively effecting movement of the disk in directions radially of the first axis, wherein the first axis is oriented relative to the resulting implant so that, when the implant is placed in the cavity in the tooth, the first axis is substantially coincident with the mesio/distal axis of the tooth.

An apparatus according to the invention, which is suitable for carrying out the inventive method, includes a rotatably supported separating disk which preferably performs substantially all of the shaping of the workpiece. One preferred form of this apparatus includes an arrangement which supports the workpiece for axial and rotational movement with respect to a first axis and which supports a tool holder for axial and rotational movement with respect to a second axis which is perpendicular to the first axis, the disk being supported on the tool holder for rotational movement about a third axis which is perpendicular to the second axis.

A key observation which has contributed to realization of the present invention is the fact that teeth have certain regions which are more prone to decay than others, namely the occlusal fissures and the proximal walls. This observation makes it possible to design implants, and to prepare the cavity accordingly, which exhibit the following features.

The inlay can be completely machined by just a disk shaped tool alone if the workpiece is gripped at one end and rotated around the mesio/distal tooth axis (namely the tooth centerline which extends through the tooth generally parallel to the row of teeth in which the tooth is disposed). Further, the grinding machine does not need more than three degrees of freedom. This basic observation makes the entire grinding operation feasible because a disk, due to a working surface many times larger than the circumference of a burr, is capable of grinding away the excess substance. Rotating the workpiece has yet another advantage: All surfaces of the workpiece will come in contact with the disk; if machining is started at an end of the blank remote from the chuck supporting it, the part can be machined all over as the disk is progressively moved axially relative to the workpiece, concluding with radially inward movement of the disk which detaches the machined inlay from the remainder of the original blank. In the case of a more complex structure, for example a crown or an onlay which extends over one or more cusps, the disk can still perform the bulk of the shaping, and a burr can be used to finish the parts inaccessible to the disk. The Applicants' U.S. Pat. No. 4,615,678 discloses a blank which can be used as a workpiece in the inventive apparatus. The blank is held in the machine by a friction grip which has a key notch to ensure a preset angular orientation. As taught in this prior application, the blank has specially designed surfaces which can be used to transmit coded data to the machine. These features are the subject of the prior U.S. patent and are only repeated here for completeness and clarity.

Since the apparatus should fit into a dental office, its size, power and noise requirements are important design constraints. A hydraulic drive has been found to best deliver the requisite speed and torque to the disk. This also allows the supply unit powering the tool to be placed outside the machine, greatly reducing the space required within the grinding chamber. It further alleviates many of the sealing problems encountered with attempts to seal electric drives and, since the water for the hydraulic drive is already in the vicinity of the machining surfaces, it can be directed so as to rinse and cool the workpiece and the tool, the rinsing and cooling being requirements which would otherwise require an additional water supply. Water driven tools are fairly well-known, including those disclosed in Oberley U.S. Pat. No. 2,697,878, Koch German Offenlegungsschrift No. 19 02 015 and Bowler U.S. Pat. No. 4,193,228, but these known devices are all of the hand-held kind and not suited for the total shaping of workpieces under consideration in an automated machine.

Only by assuring optimum speed, feed and cooling can high quality implants be machined to the desired accuracy, free of cracks and without chipping. Besides the implant itself, the diamond disk is also a relatively delicate component. It must not be bent by excessive lateral pressure, nor may the diamonds ever be heated above 150° C. because they will quickly carbonize. This set of requirements calls for an arrangement which allows monitoring of the grinding operation in some fashion.

In this case, a speed sensor which includes a magnet embedded in the turbine and a stationary pickup coil can be used. A commonly used torque sensor of the type disclosed in Nedreski U.S. Pat. No. 4,137,677 cannot be applied to this fluid drive system, since there is no back pressure in the water jet driving the double bucket turbine or Pelton wheel. Nevertheless, the velocity can be kept within a predetermined range by adjusting the feed rate. In other words, movement of the tool and workpiece can occur at a slower or faster rate, depending on the feedback information. The speed sensor can also be used to provide some machine status information, such as correct pump pressure (which relates to free running speed), and excess friction in the bearings (which results in a rapid velocity drop upon shut off of the pump). Another feature of the speed sensor is that, in combination with the specific blank, it can be used to calibrate the machine so as to compensate for wear of the tool.

BRIEF DESCRIPTION OF THE DRAWINGS

In the drawings:

FIG. 1 is a perspective view of an apparatus embodying the present invention, including a grinding mechanism, control circuitry and a water supply unit mounted on a mobile cart;

FIG. 2 is a perspective view of a blank of ceramic or composite material which can be machined by the apparatus of FIG. 1;

FIG. 4A is a side view of a tool holder and workpiece support which are components of the grinding mechanism of FIG. 1;

FIGS. 4B and 4C are diagrammatic views showing various relative operational positions of a grinding disk with respect to a workpiece in the embodiment of FIG. 1;

FIGS. 9A through 9D are respective sectional views of various implants which can be machined by the apparatus of FIG. 1;

DETAILED DESCRIPTION

Figure 3:
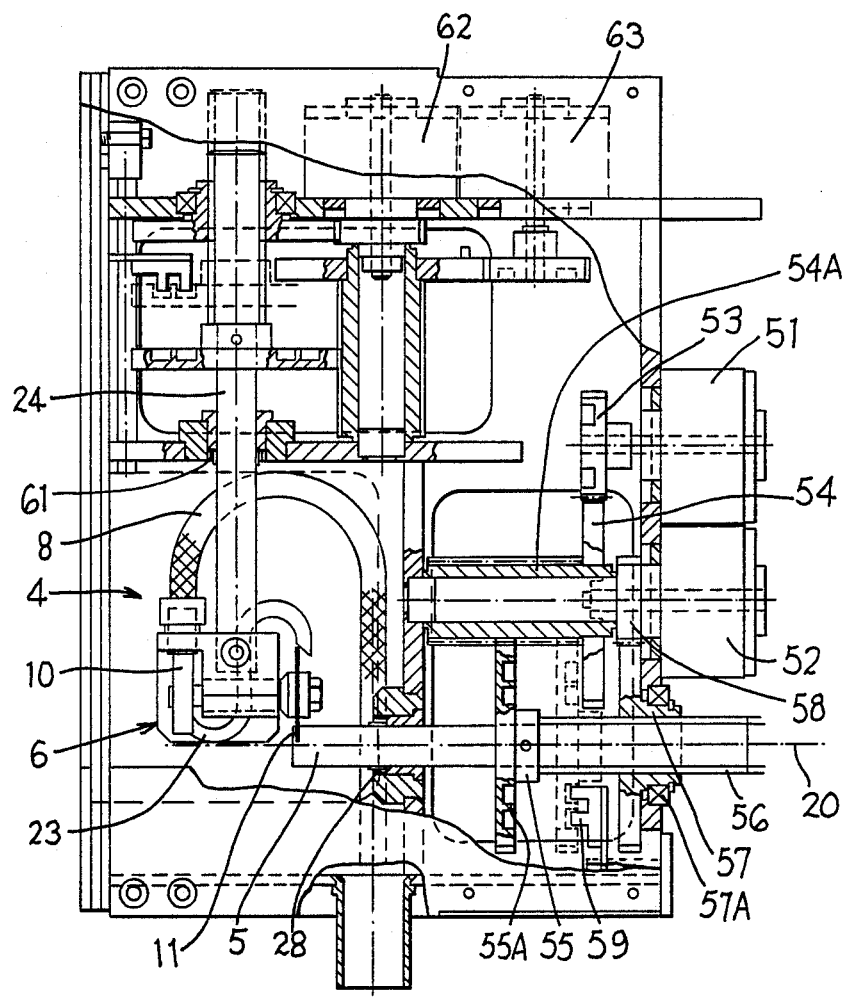
FIG. 3 is a sectional side view of the grinding mechanism of the apparatus of FIG. 1.

Referring to the drawings, FIG. 1 shows an apparatus of the same general type as that disclosed in applicants' U.S. Pat. No. 4,575,805. FIG. 2 shows a workpiece which can be machined in the apparatus of FIG. 1 and which is disclosed in applicants U.S. Pat. No. 4,615,678. The disclosure of U.S. Pat. Nos. 4,575,805 and 4,615,678 is incorporated herein by reference. The disclosure of Yamada U.S. Pat. No. 4,385,360 is also incorporated herein by reference.

In general, the apparatus disclosed in FIG. 1 includes a hand-held probe 1A which is used to optically scan a prepared three-dimensional cavity in a tooth, and an electronic circuit which uses the resulting data to cause a milling or grinding mechanism 1B to automatically machine from a blank 14 (FIGS. 1 and 2) a three-dimensional implant such as an inlay which fits precisely in and can be cemented into the cavity in the tooth. The probe 1A and electronic circuit in the preferred embodiment are structurally and functionally similar to those disclosed in U.S. Pat. No. 4,575,805, mentioned above, and are therefore not described in detail here. The present invention relates primarily to an improved method of grinding, to the improved grinding mechanism 1B, and to the integrated arrangement of the various system components in a compact manner into a single wheel-supported unit, and the following description therefore focuses on these features.

Referring to the drawings, FIG. 1 shows the externally visible parts of the apparatus according to the invention. A cabinet 1 contains all of the electrical and mechanical components except for a motor 2A for driving a fluid pump 2, and a water tank 3 and associated conduits. In the cabinet 1 there is provided a compartment 4, into which extend a cylindrical workpiece support 5 and a cylindrical shaft 24 which supports a tool holder 6. The compartment 4 is sealed from the rest of the cabinet. A transparent, vertically movable, L-shaped lid 36 provides access to the machining compartment 4 when raised into the open position shown in FIG. 1 and, when closed, acts as a silencer and as a shield which keeps fluid in the compartment 4. A double bucket turbine 10 and a thin diamond grinding disk 11 are rotatably supported on the tool holder 6 on a common rotatably supported shaft. The turbine 10 is powered by a water jet supplied from the tank 3 via pump 2 and a flexible conduit 8. The compartment 4 is drained of water by an exhaust or discharge tube 9 which returns the water to the tank 3.

Before explaining the operation of the machining mechanism itself, it should be mentioned that the cabinet 1 also contains the microprocessor-based electronic circuit which processes the three-dimensional data from the probe 1A and controls the grinding mechanism 1B. The CRT display 12 of this circuit can be used to provide a visual representation of the cavity contour and to allow verification and/or correction of stored data defining the restorative inlay.

The blank 14 preferably includes a body 15 made of a tooth-like material such as a ceramic material or a dental composite, and an attachment 16 which is made for example from aluminum and which ensures positive gripping by the chuck 5. A cylindrical gripping surface 18 is provided to ensure accurate centering, and accurate angular orientation is ensured by a key slot or groove 17 in the attachment. Adjacent to the body 15 there is a cylindrical reference surface 19 which is used to calibrate the relative positions of the tool and the workpiece. This procedure will be described below. The blank 14, once inserted into the chuck, remains gripped for the entire machining process. The very last step thereof consists of separating the machined implant, which is 99% completed, from the remaining material of the body 15. The finished implant then drops onto a screen or sieve 1C which covers the floor of the machining chamber 4 and the drain 9. The attachment 16 can if desired be ejected by an axially movable push rod which is provided in the workpiece holder 5 and which is activated upon complete axial retraction of the workpiece holder 5.

Figure 8:
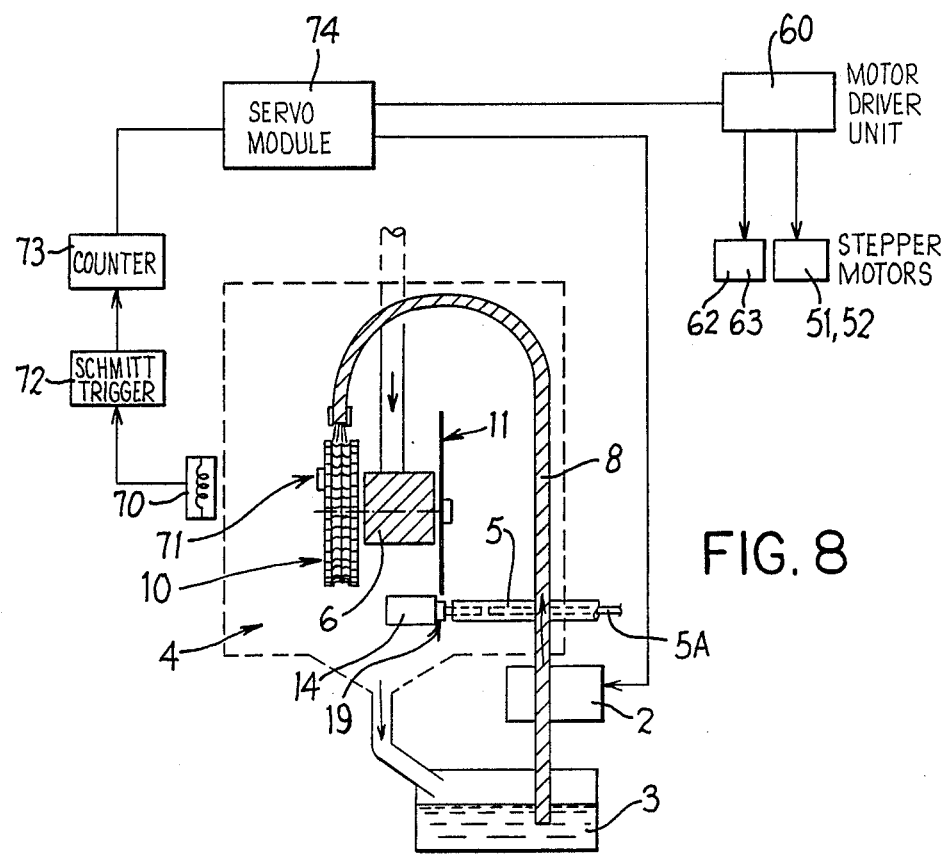
FIG. 8 is a diagrammatic view of the grinding mechanism in the embodiment of FIG. 1, and shows a fluid flow path and a speed sensing arrangement.

More specifically, referring to FIG. 8, a push rod 5A can be rotatably and axially slidably supported in a central axial opening through the workpiece holder 5. The right end of the rod 5A can be secured to a stationary member so that as the workpiece holder 5 is fully axially retracted to the right, the attachment 16 is engaged by the right end of the stationary rod 5A and is forced out of the holder 5. Alternatively, a mechanism such as an electrically actuated solenoid can be provided to effect reciprocal axial movement of the rod 5A, actuation of the solenoid causing the rod 5A to move leftwardly and force the attachment 16 out of the workpiece holder 5.

Referring to FIGS. 3 to 7, the tool holder 6 and its positioning relative to the workpiece 14 will now be described. In order to machine the materials of choice, the tools are preferably diamond coated (by electroplating) or contain diamonds (by sintering).

FIGS. 3 and 4A show the tool holder 6 equipped with a thin disk-shaped tool 11. The grinding disk 11 used in the inventive apparatus is not a common grinding wheel, which typically has a substantial axial width. Instead the grinding disk 11 has a very small axial width, and is preferably a conventional component manufactured and sold by Diametal AG, Solothurnstrasse 136, 2500 Biel 6, Switzerland, as "Trennscheiben" or "separating disks", Form No. 1A1R. These components each have a thin circular plate with a central opening therethrough, and have a platelike ring of grinding material concentrically encircling and secured to the peripheral edges of the circular plate, the ring of grinding material having an axial thickness which is slightly greater than that of the circular plate. As shown in an alternative embodiment illustrated in FIG. 5A, this tool can be complemented by a burr 21 which can also be utilized during the shaping process.

Figure 6A:
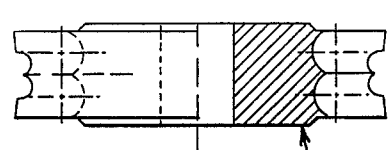
FIGS. 6A and 6B are respectively a top view and a side view of a double bucket turbine which is a component of the tool holder of FIG. 4A.
Figure 6B:
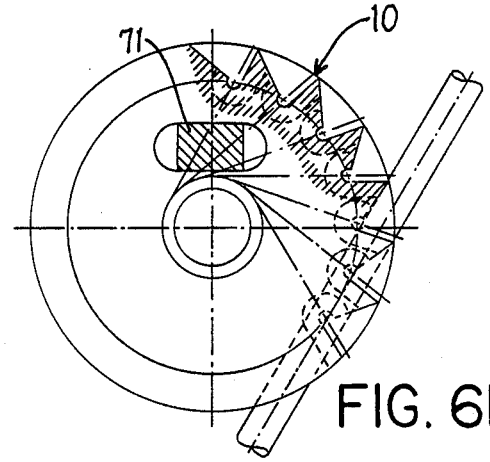
Figure 7:
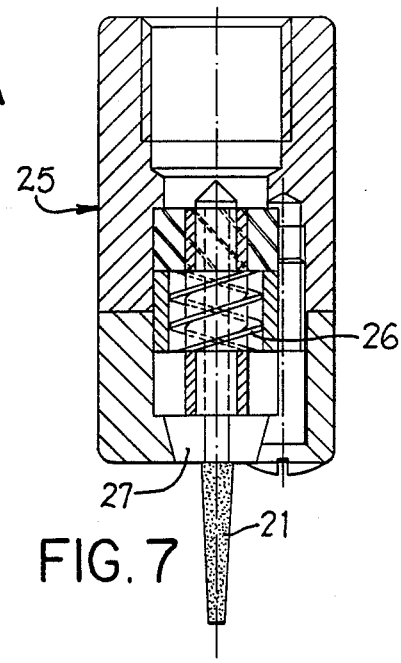
FIG. 7 is a sectional side view of an axial flow turbine which drives the burr in the embodiment of FIG. 5A.

In FIG. 4A, the turbine 10 is supplied with water via a flexible, pressure-proof hose 8 ending in a nozzle which generates a jet which strikes the turbine buckets, as shown in FIG. 6B. Another feature of the tool holder 6 is an S-shaped conduit 23, which catches part of the fluid which has passed the turbine 10 and directs it towards the machining surfaces, thereby cooling the tool and workpiece and rinsing off debris. In the alternative embodiment of FIG. 5A, the burr 21 is offset by 90° with respect to the disk 11 about the axis of a shaft 24 on which the tool holder 6' is supported. A 90° rotation of the shaft 24 can thus move the disk 11 out of contact with the workpiece and the burr 21 into contact with the workpiece, and vice-versa. The burr 21 is driven by a separate axial flow turbine 25 which is shown in section in FIG. 7 and is powered by a second pressure-proof hose (not shown) supplied with water by the pump 2, and an electrically actuated two-way valve can if desired be provided to permit water to be supplied to only a selected one of the turbines 10 and 25 at any given moment. The fluid enters the turbine 25 (FIG. 7) from the top, drives screw-shaped blades 26 provided around the burr 21, and exits through a discharge opening 27, thereby cooling and rinsing the burr and workpiece.

Figure 5A:
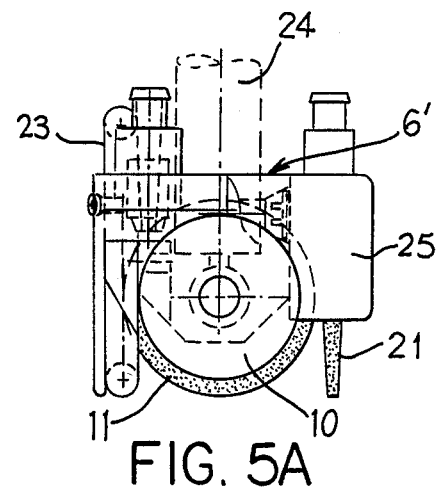
FIG. 5A is an end view of a tool holder which is an alternative embodiment of the tool holder of FIG. 4A and which has in addition to a disk a burr shaped grinding tool driven by an axial flow turbine, the two tools being arranged eccentrically to the rotational axis of the tool holder so that swivel movements can effect a change from one tool to the other.
Figure 5B:
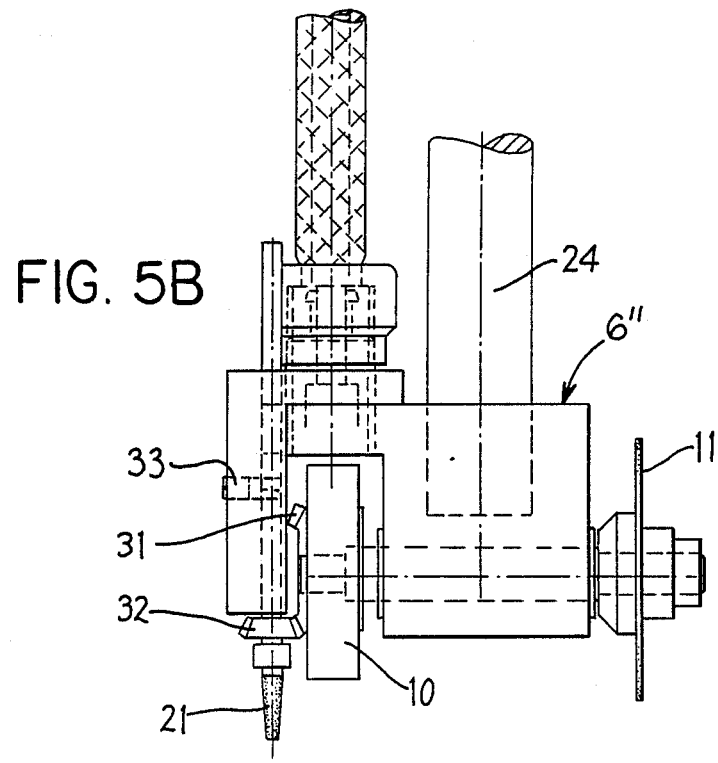
FIG. 5B is a side view of a further tool holder which is an alternative embodiment of the tool holder of FIG. 5A and in particular which has a disk and a burr located on opposite sides of the axis of rotation, the diamond burr being driven by a double bucket turbine provided for the grinding disk by means of a bevel gear.

A further alternative embodiment (FIG. 5B) is based on the same idea. Again, a disk and burr are angularly offset about the tool holder axis and can be moved into and out of operative positions by swivelling movement of the tool holder 6" about the axis of shaft 24. Note that in this embodiment a 180° rotation is needed to change tools, whereas the embodiment of FIG. 5A requires a 90° rotation. The burr 21 in FIG. 5B is driven by a large bevel gear 31. This gear 31 is fastened directly to the double bucket turbine 10, and engages a pinion 32 fastened to the burr 21. In order to uncouple the burr 21 during the time in which the disk 11 is used for machining, a two position latch mechanism 33 can be used which can yieldably resist axial movement of a shaft for the burr away from either of two axially spaced positions. To uncouple the bevel gears, the tool holder 6" is fully upwardly retracted until the upper end of a shaft for the burr engages a stationary member and pushes the burr downwardly out of the position in which the gears engage. In order to drive the burr, it can be positioned above the blank, preferrably above the reference surface 19, and the tool holder 6" can then be moved downwardly so that the burr engages the surface 19 and is moved upwardly relative to the tool holder 6" until the bevel gears 31 and 32 are again engaged.

The latch mechanism 33 can, for example, be a conventional arrangement which includes two axially spaced, circumferential grooves in the shaft for the burr 21, a ball supported in the tool holder for movement radially of the shaft, and a spring which biases the ball radially toward the shaft, the ball being disposed in a respective one of the grooves in the shaft in each of the two latched positions of the shaft.

The positional adjustment of the tool holder 6 and the workpiece support 5 will now be explained with reference to FIG. 3. The workpiece support 5, shown here without the workpiece, includes a cylindrical shaft supported by a sleeve bearing 28 equipped with a lip to seal the mechanism from the water present within the machining chamber 4. This cylindrical shaft has two degrees of freedom, namely axial and rotational movement. During the machining process these two movements can be superimposed, resulting in rotation accompanied by an axial feed of, for example, 50 micron/revolution. Two stepper motors 51 and 52 are provided, and each is equipped with an independent driver/controller. Stepper 51 rotates a gear 54 via an intermediate gear 53. This gear 54 has an elongate toothed hub 54A which drivingly engages a dog gear 55, which in turn rotates the workpiece support 5. The support 5 has at its other end a screw thread 56 which threadedly engages an internally threaded hub of a gear 57, which is rotatably supported and is fixed against axial and radial movement by means of a ball bearing 57A. A gear 58 which is secured on the shaft of stepper 52 engages the gear 57 and can thus effect axial movement of the workpiece support 5. By choosing an appropriate ratio between the number of step pulses applied to each of the two stepper motors 51 and 52, a desired feed versus rotation characteristic can be selected. To define a "home" position for the workpiece holder 5, a limit switch 59 is provided. This switch 59 is preferably a photo-electric device which senses the presence of a small, annular, axially extending rib 55A provided on the dog gear 55. This rib has, along its circumference, a small slit. This slit allows zeroing of both the axial and rotational positions. In order to zero the workpiece support 5, it is retracted axially until the limit switch 59 is interrupted by the rib in an arbitrary angular position. If the work holder is now rotated with no axial feed, the slit can be aligned with the limit switch 59 by detecting the instant upon which the light beam passes through the slit and is detected. After this "home" position has been established, all positioning of the workpiece is done by keeping track of the number of step pulses applied to the stepper motors 51 and 52.

Looking now at the tool holder 6, an identical arrangement is provided, the vertical shaft 24 being supported by a sleeve bearing 61 and the positioning of the tool holder 6 being effected by stepper motors 62 and 63.

During the machining process, the disk 11 does most and in certain cases all of the machining. As the workpiece 14 is rotated and axially advanced during machining with the disk 11, the tool holder 6 is moved only in vertical directions toward and away from the axis of the shaft of the workpiece support 5. In other words, motor 63 holds a fixed angular position and thereby causes the dog gear on shaft 24 to keep the disk 11 in an angular position where the disk axis and the axis of the shaft of the workpiece support 5 are parallel. In this position, the silhouette of the disk is its very small axial thickness, for example 0.5 mm, thereby allowing detailed contouring of the workpiece, as shown in FIGS. 4A, 4B and 4C.

The operation of the burr 21 will now be explained in greater detail. As previously discussed, a swivel motion of the tool holder 6' around the axis of the vertical shaft 24 can effect a tool change. In this operation, the shaft 24 can be considered a king pin. In order to complement the action of the disk 11, the burr 21 has the task of machining regions inaccessible to the disk. As a result of the fact that the burr 21 is located eccentrically, the burr can move along an arc substantially perpendicular to the axis of the workpiece support 5. With this in mind, a complete machining operation can be broken into four phases:

(1) The tool holder 6' and workpiece support 5 are each retracted into their respective "home" positions. They are then moved to positions in which the disk is oriented in a way so that its peripheral edge is radially aligned with the axis of the workpiece support and in contact with the end of the workpiece remote from the attachment 16.

(2) The workpiece is now rotated and moved axially to the left in FIG. 4A, and the shaft 24 is moved axially up and down in FIG. 4A, so that the disk machines the workpiece as shown in FIGS. 4B and 4C. When the disk has moved axially the full length of the implant and the implant is connected to the remaining material of the body 15 by only a small axial column a few millimeters in diameter, disk shaping is halted.

(3) The implant is now rotated into and held in an upside-down position, and the burr 21 is swivelled into an operational position. By performing sweeping arcs and axially advancing the implant at 50 microns per sweep, the burr is moved vertically in a manner which machines the underside of the implant, and in particular regions which have remained untouched by the disk. This procedure, of course, is only executed where necessary; if there are clearly no regions which the disk could not reach, this phase can be skipped. If necessary, the occlusal or top surface of the implant can also be machined by the burr. This machining of the top surface, however, is generally left to the dentist, because it involves adjustments which can best be carried out once the implant is firmly seated and the opposite tooth or teeth mesh with it (because opposing teeth and the cooperation therebetween vary from person to person).

(4) Once the burr has completed its finishing touches, the remaining column of material connecting the inlay to the remainder of the body 15 is trimmed away, preferably using the disk, so that the implant falls off, leaving at most a small nipple which the dentist can polish off.

The implant is now ready for insertion. The entire procedure requires only a few minutes and can thus occur in the dentist's office while the patient waits and while his or her local anesthesia is still effective. The restoration of a large cavity can thus be completed in a single session without the need for external laboratory work.

FIG. 8 illustrates diagrammatically the components which are used to sense the rotational velocity of the turbine, plus the related controls to form a feedback system. Besides the mechanical parts discussed above, an inductive speed detector is provided which includes a magnet 71 embedded in the turbine 10 and a pickup coil 70. The a.c. signal induced in the coil 70 is amplified in a Schmitt trigger circuit 72 and the frequency is measured by counter 73. A servo module 74 can now adjust the clock rate to a motor driver unit 60 and thus the various steppers 51, 52, 62 and 63 to keep the velocity and therefore the torque of the tool within specified ranges. This mechanism not only accelerates the grinding process, by always maintaining maximum speed, but also ensures minimum strain upon the workpiece and the diamonds.

Any tool engaged in a machining process is subject to wear. In the special case of a machine which must perform in a limited time frame, automatic compensation for the steady reduction in tool diameter has to be provided. The special blank 14 shown in FIG. 2 is equipped with the cylindrical reference surface 19, which is machined during its manufacture with a high accuracy. If, after moving the workpiece support and tool holder to their "home" positions, the disk 11 is slowly advanced radially toward the reference surface 19, a sudden drop in velocity occurs at the moment of contact therebetween. Since the diameter of the reference surface 19 is a known dimension, the exact radial position of the peripheral edge of the disk is established and any wear thereof is automatically compensated for.

Figure 10:
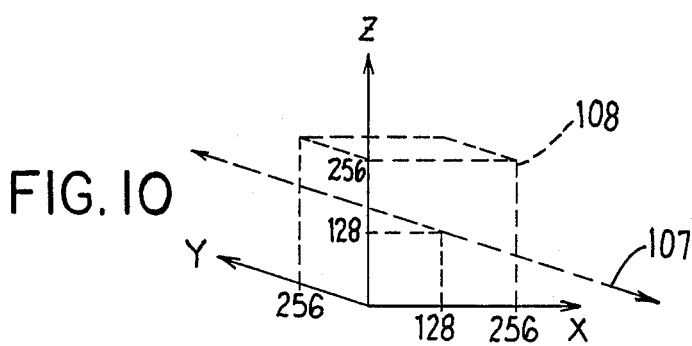
FIG. 10 is a diagram of a three-dimensional coordinate system used to define a digital representation of an implant which is to be machined by the apparatus of FIG. 1.

The manner in which the blank 14 is machined utilizing the disk 11 and the burr 21 have been briefly described above. In order to facilitate a complete understanding of this machining operation, the manner in which this machining operation is carried out will now be described in greater detail. FIGS. 9A through 9D show sectional views of typical implants which can be prepared by the inventive machining apparatus, including an inlay, small and large onlays, and a crown, respectively. For convenience, the following description is based on the onlay 106 shown in FIG. 9B. In order to digitally represent the onlay 106, so that it can be stored in a memory of the microprocessor-based electronic circuit which controls the grinding mechanism 1B, a three-dimensional coordinate system is used, as shown in FIG. 10. In particular, the coordinate system consists of perpendicular X, Y and Z axes, and a region 108 of interest is a cube having three edges coincident with the three axes. Each unit of length along each axis is 50 microns (0.05 millimeter) in the preferred embodiment, and each side of the cube is 256 units, or in other words 12.8 millimeters in length. A centerline 107 extends centrally through the cubic region parallel to the Y axis and is the locus of points for which $X=128$ and $Z=128$. The desired implant can be conceptionally positioned within the cubic region 108, and a plurality of points on the surface of the implant 106 can each be represented by a unique X, Y, Z coordinate.

The memory of the electronic circuit includes a 256 × 256 location array, the rows of the array corresponding to units along the X axis and the columns of the array corresponding to units along the Y axis, and each location in the array holds an 8-bit digital number which defines a displacement along the Z axis. Thus, each location in the array can define a unique point within the cubic region 108.

Figure 11:
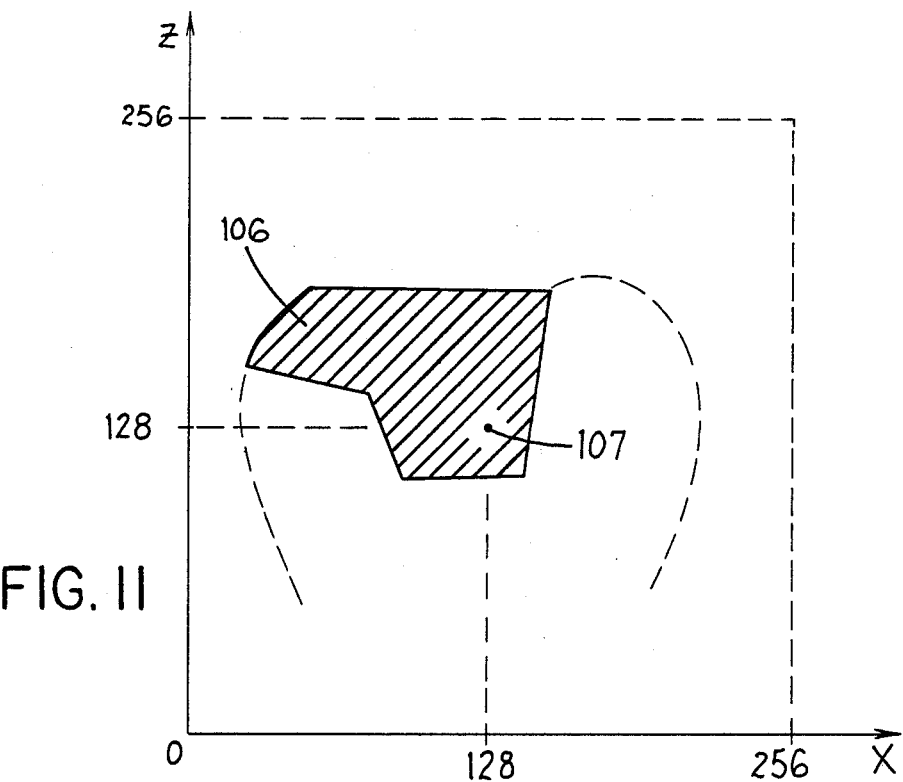
FIG. 11 shows a view of the implant of FIG. 9B within the coordinate system of FIG. 10.
Figure 12:
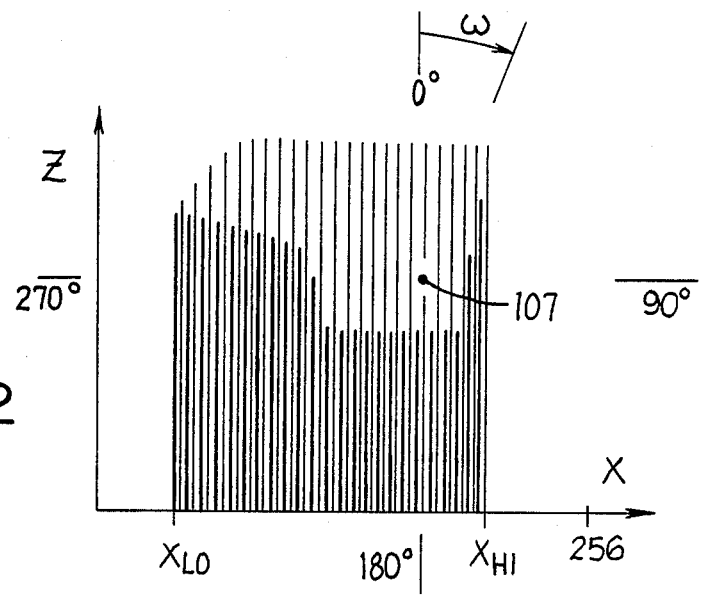
FIGS. 12 and 13 are respective graphical views of digitized representations of the implant shown in FIG. 11.
Figure 13:
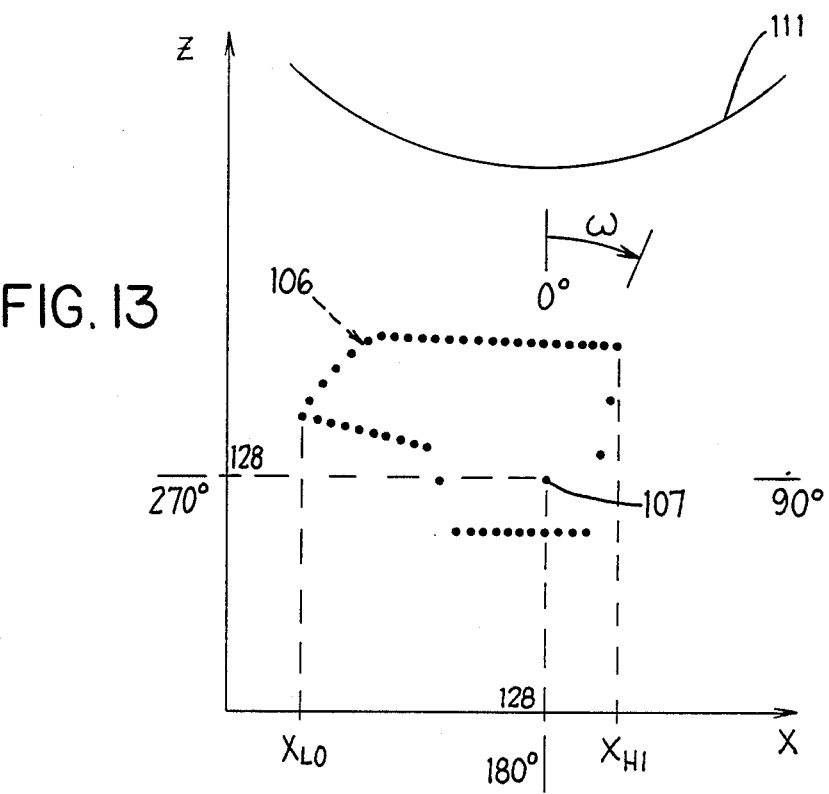

FIG. 11 shows a sectional view of the implant 106 which is defined by a plane perpendicular to the Y axis at a given location along the Y axis, and data regarding this "slice" of the implant is stored in the corresponding column of the array in the memory of the electronic circuit in the following manner. For a given column of the array in memory corresponding to the given location along the Y axis of the onlay slice shown in FIG. 11, the locations in the column from even numbered rows store data defining points on the underside of the onlay 106, and the locations in the column from odd numbered rows store data defining points on the upper surface of the onlay 106. This is shown graphically in FIG. 12 for the slice depicted in FIG. 11, where the vertical bars represent the displacements along the Z axis stored in the various locations in the given column of the array. Of course, for purposes of clarity in FIG. 12, the number of vertical bars illustrated is much less than the actual number of locations in the column containing displacements. It will be noted that the upper ends of the shorter vertical lines in FIG. 12 define a line corresponding to the underside of the onlay 106 in FIG. 11, and the upper ends of the longer vertical lines in FIG. 12 define a line which corresponds to the upper surface of the onlay 106 in FIG. 11. The left and right ends of the slice of the onlay are located at points $X_{lo}$ and $X_{hi}$, and locations in the given column of the array for which X is less than $X_{lo}$ or greater than $X_{hi}$ contain the value zero to indicate that there is no corresponding point on the surface of the onlay. FIG. 13 corresponds to FIG. 12 but is a plot of the actual points defined by the stored information, and more clearly shows the fact that the memory can in fact store an accurate representation of the slice of the onlay shown in FIG. 11. The columns of the array each represent a respective slice of the onlay, adjacent slices being spaced by 50 microns, and the array as a whole thus contains an accurate representation of the entire external surface of the onlay 106.

Referring again to FIG. 12, the generation of the data stored in the memory array will now be briefly described. The scanhead 1A (FIG. 1) scans the prepared cavity in the tooth, and then the electronic circuit produces in the memory array the digital representation of the surfaces of the cavity, which surfaces correspond to the underside of the desired onlay 106. Thus, referring to FIG. 12, the points represented by the shorter vertical line are generated and stored in the array using the scanhead 1A. The manner in which this is done is disclosed in more detail in above-mentioned U.S. Pat. No. 4,575,805, and is therefore not described in further detail here. The top surface of the onlay can be defined in several different ways. For example, referring to FIGS. 1 and 13, if the points generated by the scanhead 1A and representing the underside of a slice of the onlay are displayed on the screen of the CRT 12 in a format similar to that shown in FIG. 13, the operator of the system can use a conventional joy-stick or similar device to draw a line on the screen representing the desired upper surface of that slice of the onlay, and this line can then be digitized and stored in the array by the microprocessor-based electronic circuit in a conventional manner. It would alternatively be possible to have the microprocessor in the electronic circuit automatically generate an appropriate line utilizing basic curve fitting techniques. Either such approach, or an equivalent technique, is suitable for purposes of the present invention.

The manner in which the information in the memory array is used to control machining of the blank 14 will now be described, beginning with the grinding phase utilizing the disk 11. Referring to FIGS. 10 and 13, the centerline 107 is treated as being coincident with the axis 20 (FIG. 3) about which the blank 14 is rotated, the X axis extending horizontally and the Z axis vertically, and the cubic region 108 is conceptionally assumed to be located within the blank. For purposes of convenience, a 0° position of the rotatable blank 14 will be defined as the position in which the groove or slot 17 (FIG. 2) therein faces upwardly and in which the inlay being machined therefrom is in the upright orientation shown in FIGS. 9B and 13. As described above, machining of the blank 14 using the disk 11 begins at the free end of the blank 14 and proceeds axially toward the attachment 16 (FIG. 2). The blank 14 is indexed axially in steps of 50 microns. In particular, for a given axial position of the blank 14, the blank 14 is rotated through 360° while the disk 11 is moved vertically in order to machine the external surface of an axial slice of the blank, the blank 14 is then moved axially by a discreet step of 50 microns, after which it is again rotated 360° while the disk 11 is moved vertically in order to machine the external surface of a further axial slice of the blank. With respect to the array stored in the memory of the electronic circuit, and the fact that the Y axis of the coordinate system is parallel to the axis 20 of the blank, the successive 50 micron axial movements of the blank correspond to respective columns in the array. Thus, as the blank 14 is rotated in a given axial position, the appropriate movement of the disk 11 is determined by evaluating the data stored in the various locations in the corresponding column of the array.

More specifically, referring to FIG. 13, it is assumed that the blank 14 is initially in the 0° position. As described above, the diameter of the disk 11 will decrease with time due to wear, but the actual diameter at the current time can be determined as described above, in particular by bringing the disk into contact with the reference surface 19 on the attachment 16 of the blank. Thus, since the actual diameter of the disk 11 is known, a curve 111 can be mathematically calculated in the X-Z coordinate system which represents the outer edge of the disk and has a curvature corresponding to the actual diameter of the disk, and the curve can be positioned within the X-Z coordinate system so that its centerpoint is directly above the centerline 107 and the spacing of the centerpoint from the centerline 107 is equal to the actual distance between the axis of the disk 11 and the axis 20 of the blank 14. The vertical distance between the curve 111 and each of the points representing the onlay 106 is then calculated mathematically. The smallest of these calculated distances represents the distance which the disk 11 can be moved vertically downwardly without grinding away a portion of the blank which is not supposed to be machined. The disk 11 is then moved downwardly and then upwardly this distance, after which the blank 14 is indexed rotationally by an amount which, in the preferred embodiment, is 360°/256°. The points graphed in FIG. 13 and representing the desired onlay can be mathematically rotated about the centerline 107 using standard equations. In particular, a point having the coordinates (x, z) will have a rotated position of (x', z'), where:

$$x' = (x-128)\cos\omega - (z-128)\sin\omega, \text{ and}$$
$$z' = (x-128)\sin\omega - (z-128)\cos\omega,$$

where $\omega$ is the angle of rotation, as shown in FIG. 13. The vertical distance between the curve 111 and the rotated position of each of the points is then carried out, the smallest of the calculated distances being the minimum distance which the disk 11 can be moved downwardly without machining away material which is not supposed to be machined. The disk 11 is then moved downwardly this distance and is again retracted upwardly, the blank 14 is rotated another 360°/256°, and so forth. Each time a full 360° rotation is completed, the blank is advanced axially by 50 microns, and the data in the next column of the array is used for calculations.

For simplicity, the foregoing discussion explains that the disk 11 is retracted upwardly before each rotational movement of the blank 11. As a practical matter, the upward retraction of the disk 11 can in fact be avoided by calculating, prior to each rotational movement of the blank 14, the lowest permissible position of the disk 11 for the next angular position of the blank 14. If such position is above the current position of the disk 11, the disk 11 is moved upwardly to this position and the blank 14 is then rotated, whereas if such position is below the current position of the disk, the blank 14 is first rotated and then the disk is moved to such position.

Also, as a practical matter, the blank can in fact be axially advanced in a continuous manner as it is rotated, at a rate of 50 microns per revolution, without any significant adverse effect on the resulting implant.

Also, the foregoing discussion assumed that the disk 11 has an axial thickness of only 50 microns, so that it can machine each slice independently. The outer edge of the disk used in the preferred embodiment actually has a thickness of about 500 microns. Thus, when calculating the minimum distance which the disk 11 can be moved downwardly, it is necessary to find the smallest permissible distance between the curve 111 and the points in ten adjacent columns of the array, but the basic calculations required are identical to those described above.

When machining a simple implant, for example the inlay shown in FIG. 9A, the disk 11 can completely machine the requisite inlay, because there are no points on the surface of the inlay which the disk 11 cannot reach. In contrast, in onlays of the type shown in FIGS. 9B and 9C, there are points 113 and 114 on the surface of the onlay which the disk cannot reach, due to the diameter of the disk. Accordingly, after machining using the disk 11 in the manner described above, and in order to produce the correct shape in regions such as at the point 113, machining is carried out using the burr 21 (FIG. 5B) in the manner described below. In this respect, it should be noted that it is not necessary for the electronic circuit to keep track of which regions in fact cannot be machined by the disk. The procedure described above automatically ensures that the disk machines all material it can reach but no more, and the procedure described below ensures that the burr automatically machines all excess material not machined by the disk. The dentist can easily be trained to recognize whether or not he has prepared a cavity requiring an implant which can be machined entirely with the disk, which is important if he or she has the embodiment of the inventive apparatus which does not have the burr.

To initiate machining with the burr 21, the tool holder 6' is rotated the requisite angular distance about its axis so as to move the disk 11 out of a machining position and the burr 21 into a machining position. Simultaneously, the blank 111 is rotated about the axis 20 to its 180° position, or in other words the position in which the onlay 106 being machined is upside down. Utilizing axial movement of the blank 14 and rotational movement of the tool holder 6, the burr 21 is successively moved to positions which each correspond to the x-y coordinates of a respective location in the memory array storing a value representing a point on the underside of the onlay, and the burr 21 is then moved downwardly a distance corresponding to the stored z-axis value. Where the disk has already properly machined the requisite surface, the burr will have no effect, but in regions the disk was unable to reach, the burr will machine away excess material in order to produce the required surface.

If the size of the lower end of the burr is sufficiently large, it will be necessary to account for the fact that in any given position the lower end of the burr will actually be covering an area corresponding to several of the locations in the array, and the downward movement of the burr would thus have to be based on the smallest of the numbers stored in these locations. The lower end of the burr is preferably as small and as pointed as possible, in order to avoid or minimize the need for such compensation. As described above, the movement of the burr relative to the blank to successive positions corresponding to respective locations in the memory array is effected by rotating the tool holder 6 through a predetermined arc in a first direction, then moving the blank 14 a small distance axially, then rotating the tool holder 6 in the opposite direction through the predetermined arc, again indexing the blank 14 in the same axial direction, then rotating the tool holder 6 in the first direction through the predetermined arc, and so forth. Each axial movement of the blank corresponds to movement from one column of the memory array to an adjacent column, and if the tool holder 6' moved the burr 21 linearly, instead of arcuately, transverse movement of the burr would correspond to movement along the columns of the array. Since the burr is in fact moved along an arcuate path of movement, a given arcuate sweep will in fact move the burr through positions corresponding to locations in more than one column of the array. Since the radial distance of the burr from the axis of the tool holder is predetermined, however, the path of the burr, or the precise sequence in which the locations of the array will be accessed as a result of the movement of the burr, can be predetermined and stored in the memory in tabular form.

In the preferred embodiment, the top surface of the onlay 106 (FIG. 9B) will typically not have any regions which have not been properly machined by the disk, and the preferred method and apparatus thus do not use the burr 21 to do any machining on the top surface of the onlay 106. Once the onlay 106 has been cemented into the cavity in the tooth, the dentist will typically use a conventional hand-held grinding device to apropriately shape the top of the onlay and to polish the onlay and adjacent regions of the tooth so that they smoothly conform with each other. Nevertheless, it is within the scope of the invention for the burr to machine the top surface of the onlay.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A method of fabricating a custom shaped dental implant which has an external surface, comprising the steps of removably supporting a workpiece blank on a workpiece support, and then completely machining said implant, including all of said external surface thereof, from said prefabricated workpiece blank without removing said workpiece blank from said workpiece support during the machining of said implant, said machining step terminating with the step of detaching said implant from a portion of said workpiece blank remaining on said workpiece support.

2. A method according to claim 1, where said machining step is carried out using a separating disk having a small axial thickness.

3. A method according to claim 1, wherein said machining step includes the step of rotating said workpiece about an axis which corresponds to a mesio/distal axis of the tooth or teeth under reconstruction, and the step of moving the tool radially with respect to said axis.

4. A method of machining from a workpiece a dental implant having a three-dimensional external surface, comprising the steps of rotating said workpiece about a first axis, and machining the entire external surface of said implant by moving a machining part relative to said rotating workpiece in a direction parallel to said first axis and by selectively effecting movement of said machining part in directions radially of said first axis.

5. A method of fabricating a custom-shaped dental implant for an irregularly shape cavity in a tooth, comprising the steps of rotating a prefabricated workpiece blank about an axis of rotation and machining therefrom said implant, said machining step including the step of machining axially facing external surfaces on opposite sides of said implant which are each intersected by said axis of rotation.

6. A method according to claim 5, wherein said machining step includes the step of physically separating the implant from a remaining portion of said workpiece blank.

7. A method according to claim 4, wherein said threedimensional external surface is circumferentially irregular, and wherein said step of effecting radial movement of said machining part includes the step of effecting a significant amount of radial movement thereof in relation to a predetermined angular movement of said workpiece which is a small portion of one revolution thereof.

8. A method according to claim 4, wherein said first axis is oriented relative to the implant so as to be substantially coincident with a mesio/distal axis of the tooth when the implant is placed in the cavity in the tooth.

9. A method according to claim 4, including the steps of utilizing as said machining part a grinding tool, and rotating said grinding tool about a second axis at a speed substantially greater than the speed at which said workpiece is rotated.

10. A method according to claim 9, including the steps of utilizing as said grinding tool a grinding disk of small axial thickness, and orienting said second axis parallel to said first axis.

11. A method according to claim 9, including the step of maintaining the rotational velocity of said grinding tool within a predetermined velocity range.

12. A method according to claim 10, including prior to said machining of said workpiece the steps of securing to said workpiece an attachment which has at a predetermined location with respect to said first axis a reference surface, rotating said grinding disk while moving said grinding disk toward said reference surface and while simultaneously monitoring the rotational velocity of said grinding disk, the rotational velocity of said grinding disk decreasing when said grinding disk contacts said reference surface, and responding to a decrease in the rotational velocity of said grinding disk by recording the current location of said second axis and then calculating the distance from said second axis to said reference surface in order to accurately determine the actual current diameter of said grinding disk.

13. A method according to claim 10, wherein said machining step includes the steps of moving said grinding disk to a position spaced from said workpiece, rotating a further grinding tool about a third axis, and machining material from said workpiece using said further grinding tool.

14. A method according to claim 13, including the steps of selecting said further grinding tool to have a small effective grinding surface, and halting said rotating of said workpiece during said machining with said further grinding tool.

15. A method according to claim 14, including the steps of utilizing a burr as said further grinding tool, orienting said third axis to be in a plane perpendicular to said first axis, and selectively effecting movement of said burr in directions parallel to said third axis while moving said burr through an arc concentric to a fourth axis which is parallel to and spaced from said third axis.

16. A method according to claim 15, including the step of providing first and second elongate support members which are respectively coincident with said first and fourth axes and which are each capable of rotational and axial movement, releasably securing said workpiece to an end of said first support member, and supporting said grinding disk and said further grinding tool on said second support member.

17. A method according to claim 13, including the step of directing a jet of fluid onto a turbine coupled to at least one of said grinding tools in order to effect said rotation of the grinding tool.

18. A method according to claim 17, including the step of causing at least a portion of the fluid directed onto the turbine to thereafter flow onto the workpiece to cool and rinse it.

19. A method according to claim 4, wherein said machining step includes as a final step the step of using said machining part to physically detach said implant from a remaining portion of said workpiece.

20. A method according to claim 1, including the steps of supporting said workpiece support for rotation about an axis of rotation extending through said workpiece blank, said workpiece support being located at one axial end of said blank, and supporting a rotating tool for movement relative to said workpiece blank in directions axially and radially of said axis of rotation; and wherein said machining step includes the steps of: rotating said workpiece support and said blank thereon in one direction about an axis of rotation, simultaneously moving said workpiece blank parallel to said axis of rotation relative to said tool from a first axial location to a second axial location, said axial movement of said blank being synchronized to rotation thereof so that said blank moves a predetermined axial distance for each 360° revolution of said blank, and simultaneously moving said tool radially inwardly and outwardly in synchronism with said rotation and axial movement of said blank so as to machine from said blank said implant having said external surface thereon, wherein at a first axial end of said implant which is axially further from said workpiece support than a second axial end thereof said tool is moved radially inwardly to said axis of rotation, and wherein at said second axial end of said implant said tool is moved radially so as to leave a small column extending axially between said implant and said portion of said blank on said workpiece support, and thereafter causing said tool to machine away said column in order to detach said implant from said portion of said blank.

21. A method according to claim 20, wherein said tool is a separating disk supported for rotation about an axis extending parallel to said axis of rotation of said blank, said disk having a speed of rotation substantially greater than the speed at which said workpiece support and said blank thereon are rotated.

22. A method according to claim 21, including immediately prior to said step of machining away said column the steps of: stopping the rotation of said workpiece support when said workpiece support is in a predetermined angular position; and thereafter machining a small amount of material from at least one selected location on said implant using a rotating burr.

23. A method according to claim 22, including after said step of machining with said burr and prior to said step of machining away said column with said tool the step of causing said workpiece support to resume said rotation in said one direction.

* * * * *